United States Patent
Delaney et al.

(10) Patent No.: US 6,730,063 B2
(45) Date of Patent: May 4, 2004

(54) CATHETER DEVICES AND METHODS FOR THEIR USE IN THE TREATMENT OF CALCIFIED VASCULAR OCCLUSIONS

(75) Inventors: Dave Delaney, Menlo Park, CA (US); Peter Johansson, Menlo Park, CA (US); Brent R. Constantz, Menlo Park, CA (US)

(73) Assignee: Corazon Technologies, Inc., Menlo Park, CA (US)

( * ) Notice: Subject to any disclaimer, the term of this patent is extended or adjusted under 35 U.S.C. 154(b) by 8 days.

(21) Appl. No.: 09/911,529

(22) Filed: Jul. 23, 2001

(65) Prior Publication Data

US 2001/0041865 A1 Nov. 15, 2001

Related U.S. Application Data

(63) Continuation of application No. 09/425,826, filed on Oct. 22, 1999, now Pat. No. 6,290,689.

(51) Int. Cl.[7] .................................................. A61M 3/00
(52) U.S. Cl. .................... 604/173; 604/264; 604/96.01; 604/43
(58) Field of Search ........................ 604/101.01, 101.04, 604/101.05, 163, 27, 164.01, 173, 164.08, 164.09, 164.1, 164.11, 96.01, 93.01, 101.03, 102.01, 102.03, 507–509, 264, 183, 912, 43; 606/192–194, 198, 159

(56) References Cited

U.S. PATENT DOCUMENTS 4,329,994 A 5/1982 Cooper
4,445,892 A 5/1984 Hussein et al.

(List continued on next page.)

FOREIGN PATENT DOCUMENTS

WO WO97/44082 11/1997

OTHER PUBLICATIONS

Hargrove III et al. (Dec. 1982), "Treatment of Acute Peripheral Arterial and Graft Thromboses with Low–Dose Streptokinase," *Surgery*; vol. 92(6):981–993.

Koltun et al. (Aug. 1987), "Thrombolysis in the Treatment of Peripheral Arterial Vascular Occlusions," *Arch Surg*, vol. 122:901–905.

Olin et al. (Nov. 1988), "Thrombolytic Therapy in the Treatment of Peripheral Arterial Occlusions," *Annals of Emergency Medicine*, vol. 17:1210/125–1215/130.

Rickard et al. (Dec. 1997), "Limitations of Intra–Arterial Thrombolysis," *Cardiovascular Surgery*, vol. 5(6):634–640.

*Primary Examiner*—Brian L. Casler
*Assistant Examiner*—Jennifer Maynard
(74) *Attorney, Agent, or Firm*—Bret E. Field; Bozicevic, Field & Francis LLP

(57) ABSTRACT

Catheter devices and methods for their use in enhancing fluid flow through a vascular site occupied by a vascular occlusion are provided. The subject catheter devices include at least a first, second and third lumen, where: (a) the first lumen is used for delivery of an acidic dissolution solution to the vascular site; (b) the second lumen is used for delivery of a buffer solution to the vascular site; and (c) the third lumen is used for removal of fluid from the vascular site. In many preferred embodiments, the first, second and third lumens are coaxial. In practicing the subject methods, the vascular site is flushed simultaneously with an acidic dissolution fluid and a buffer solution, where flushing is carried out in a manner such that only a surface of the vascular occlusion is contacted with the acidic dissolution fluid and the remainder of the vascular site is not contacted with fluid having a pH that is lower than about 4. Flushing is carried out in this manner for a period of time sufficient for fluid flow through the vascular site to be enhanced, e.g. increased or established. The subject catheter devices and methods find use in the treatment of a variety of different vascular diseases characterized by the presence of calcified vascular occlusions, including peripheral and coronary vascular diseases.

13 Claims, 12 Drawing Sheets

U.S. PATENT DOCUMENTS

| | | | |
|---|---|---|---|
| 4,573,966 A | * | 3/1986 | Weikl et al. ................. 604/509 |
| 4,610,662 A | | 9/1986 | Weikl et al. |
| 4,636,195 A | * | 1/1987 | Wolinsky .................... 604/509 |
| 4,655,746 A | | 4/1987 | Daniels et al. |
| 4,681,104 A | * | 7/1987 | Edelman ........................ 606/7 |
| 4,690,672 A | | 9/1987 | Veltrup |
| 4,824,436 A | | 4/1989 | Wolinsky |
| 4,838,881 A | | 6/1989 | Bennett |
| 4,911,163 A | | 3/1990 | Fina |
| 4,976,733 A | | 12/1990 | Girardot |
| 5,059,178 A | | 10/1991 | Ya |
| 5,090,960 A | | 2/1992 | Don Michael |
| 5,149,330 A | | 9/1992 | Brightbill |
| 5,167,623 A | | 12/1992 | Cianci et al. |
| 5,167,628 A | | 12/1992 | Boyles |
| 5,195,955 A | | 3/1993 | Don Michael |
| 5,207,648 A | * | 5/1993 | Gross ......................... 604/164 |
| 5,222,941 A | | 6/1993 | Don Michael |
| 5,370,609 A | | 12/1994 | Drasler et al. |
| 5,380,284 A | | 1/1995 | Don Michael |
| 5,443,446 A | | 8/1995 | Shturman |
| 5,462,529 A | * | 10/1995 | Simpson et al. ........ 604/101.04 |
| 5,489,271 A | * | 2/1996 | Andersen .................... 604/102 |
| 5,496,267 A | | 3/1996 | Drasler et al. |
| 5,542,937 A | | 8/1996 | Chee et al. |
| 5,624,396 A | * | 4/1997 | McNamara et al. ...... 604/93.01 |
| 5,674,198 A | * | 10/1997 | Leone ........................ 604/101 |
| 5,681,336 A | * | 10/1997 | Clement et al. ............ 606/159 |
| 5,728,123 A | | 3/1998 | Lemelson et al. |
| 5,749,858 A | * | 5/1998 | Cramer ....................... 604/164 |
| 5,755,682 A | * | 5/1998 | Knudson et al. ............... 604/8 |
| 5,785,675 A | | 7/1998 | Drasler et al. |
| 5,833,650 A | | 11/1998 | Imran |
| 5,947,985 A | * | 9/1999 | Imran ......................... 606/159 |
| 6,013,068 A | | 1/2000 | Spiegelhalter |
| 6,022,336 A | * | 2/2000 | Zadno-Azizi et al. ......... 604/96 |
| 6,083,198 A | * | 7/2000 | Afzal .................... 604/101.01 |
| 6,146,373 A | * | 11/2000 | Cragg et al. ................ 604/523 |
| 6,290,689 B1 | * | 9/2001 | Delaney et al. ............. 604/507 |

* cited by examiner

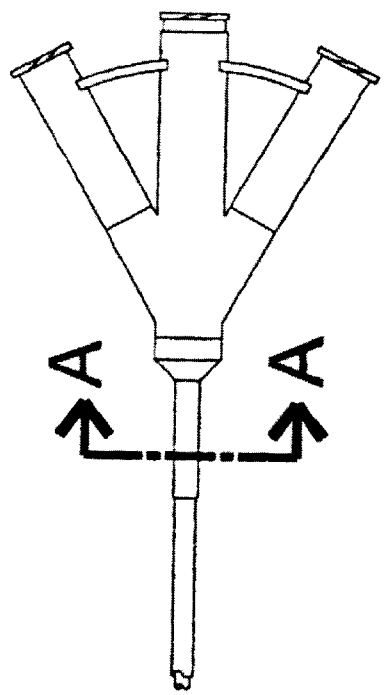
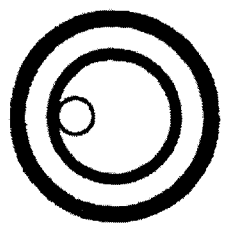
FIG. 13
Section A-A
Not to scale

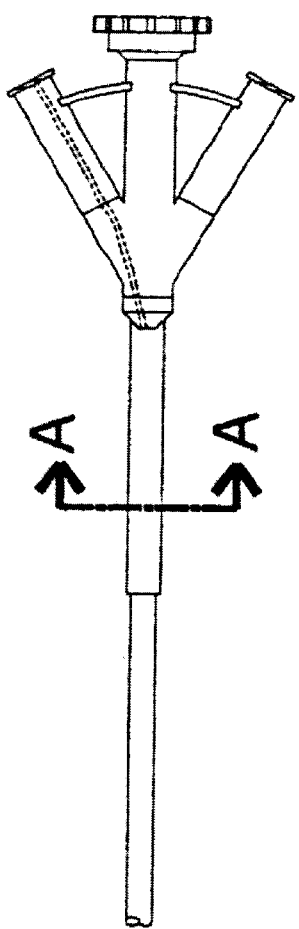
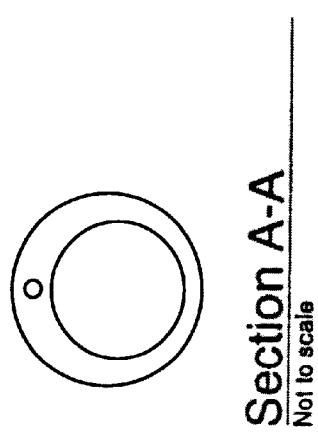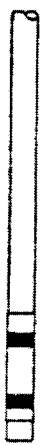
FIG. 14
Section A-A
Not to scale

CATHETER DEVICES AND METHODS FOR THEIR USE IN THE TREATMENT OF CALCIFIED VASCULAR OCCLUSIONS

CROSS-REFERENCE

This application is a continuation of Ser. No. 09/425,826, filed Oct. 22, 1999 now U.S. Pat. No. 6,290,689, which is incorporated herein by reference in its entirety and to which application we claim priority under 35 USC § 120.

INTRODUCTION

1. Technical Field

The field of this invention is vascular disease, particularly vascular diseases characterized by the presence of calcified vascular occlusions.

2. Background of the Invention

Vascular occlusions, which may be partial or total occlusions, play a prominent role in many types of vascular disease. Many vascular occlusions encountered in the treatment of vascular disease are characterized by having a mineral component, i.e. they are calcified. Calcified vascular occlusions, both partial and total, are found in both peripheral and coronary vascular disease A variety of different protocols have been developed for treating vascular diseases characterized by the presence of partial or total occlusions. Such treatment methodologies generally involve mechanical removal or reduction of the size of the occlusion, and include: bypass surgery, balloon angioplasty, mechanical debridement, atherectomy, and the like.

Despite the plethora of different treatment strategies that have been developed for the treatment of vascular diseases associated with vascular occlusions, there are disadvantages associated with each technique, such as tissue damage, invasiveness, etc. For example, restenosis is a common complication that results in arteries in which occlusions have been mechanically removed.

Calcified vascular occlusions pose significant challenges to currently employed treatment methodologies. For example, where the target vascular occlusion is a total occlusion, it is difficult if not impossible to pass a guidewire through the occlusion, which step is required for many of the currently used procedures. While bypass grafts are sometimes available as alternatives in such instances, bypass procedures have their own risks and complications. Furthermore, if there is no appropriate anastomosis site available, amputation is often the only alternative.

As such, there is continued interest in the development of endovascular methods of treating vascular occlusions. Of particular interest would be the development of methods and devices suitable for use in the treatment of calcified vascular occlusions.

Relevant Literature

U.S. patents of interest include: U.S. Pat. Nos. 4,445,892; 4,573,966; 4,610,662; 4,636,195; 4,655,746; 4,690,672; 4,824,436; 4,911,163; 4,976,733; 5,059,178; 5,090,960; 5,167,628; 5,195,955; 5,222,941; 5,370,609; 5,380,284; 5,443,446; 5,462,529; 5,496,267; 5,785,675; and 5,833,650. See also: Koltun et al., Arch. Surg. (August 1987) 122:901–905; Olin et al., Ann. Emerg. Med. (November 1988) 17:1210–1215; Hargrove et al., Surgery (December 1982) 92:981–993; and Rickard et al., Cardiovascular Surg. (December 1997) 5:634–640. See also PERIPHERAL ENDOVASCULAR INTERVENTIONS, $2^{nd}$ ed. (White & Fogarty eds., Springer, N.Y.)(1996) pp 565–576.

SUMMARY OF THE INVENTION

Multi-lumen catheter devices and methods for their use in enhancing fluid flow through a vascular site occupied by a vascular occlusion are provided. The subject catheter devices include at least a first, second and third lumen, where: (a) the first lumen is used for delivery of an acidic dissolution solution to the vascular site; (b) the second lumen is used for delivery of a buffer solution to the vascular site; and (c) the third lumen is used for removal of fluid from the vascular site. In many preferred embodiments, the first, second and third lumens are coaxial. In practicing the subject methods, the vascular site is flushed simultaneously with an acidic dissolution fluid and a buffer solution, where flushing is carried out in a manner such that only a surface of the vascular occlusion is contacted with the acidic dissolution fluid and the remainder of the vascular site is not contacted with fluid having a pH that is lower than about 4. Flushing is carried out in this manner for a period of time sufficient for fluid flow through the vascular site to be enhanced, e.g. increased or established. Also provided are systems and kits comprising the subject catheter devices. The subject catheter devices, kits, systems and methods find use in the treatment of a variety of different vascular diseases characterized by the presence of calcified vascular occlusions, including peripheral and coronary vascular diseases.

BRIEF DESCRIPTION OF THE FIGURES

FIG. 13 provides another view of a partial occlusion catheter of the catheter systems of the subject invention.

FIG. 14 provides another view of an aspiration or irrigation catheter of the catheter systems of the subject invention.

DESCRIPTION OF THE SPECIFIC EMBODIMENTS

Figure 1A:
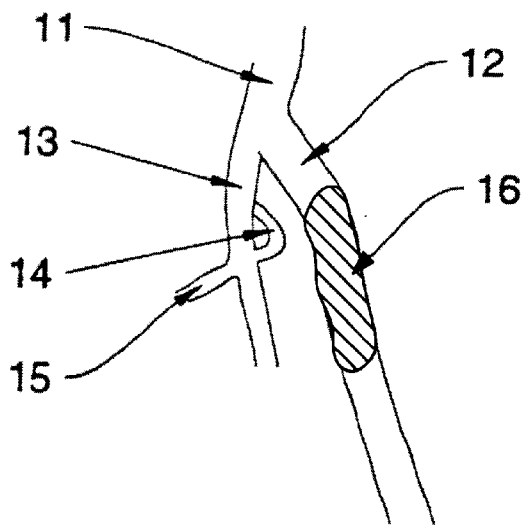
FIGS. 1A & 1B provide views of a totally occluded and partially occluded vascular site, respectively.

Multi-lumen catheter devices and methods for their use in enhancing fluid flow through a vascular site occupied by a vascular occlusion are provided. The subject catheter devices include at least a first, second and third lumen, where: (a) the first lumen is used for delivery of an acidic dissolution solution to the vascular site; (b) the second lumen is used for delivery of a buffer solution to the vascular site; and (c) the third lumen is used for removal of fluid from the vascular site. In many preferred embodiments, the first, second and third lumens are coaxial. In practicing the subject methods, the vascular site is flushed simultaneously with an acidic dissolution fluid and a buffer solution, where flushing is carried out in a manner such that only a surface of the vascular occlusion is contacted with the acidic dissolution fluid and the remainder of the vascular site is not contacted with fluid having a pH that is lower than about 4. Flushing is carried out in this manner for a period of time sufficient for fluid flow through the vascular site to be enhanced, e.g. increased or established. Also provided are systems and kits comprising the subject catheter devices. The subject catheter devices, kits, systems and methods find use in the treatment of a variety of different vascular diseases characterized by the presence of calcified vascular occlusions, including peripheral and coronary vascular diseases.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms [a,] [an,] and [the] include plural reference unless the context clearly dictates otherwise. Unless defined otherwise all technical and scientific terms used herein have the same meaning as commonly understood to one of ordinary skill in the art to which this invention belongs.

Catheter Devices-general Features

As summarized above, the subject invention provides multi-lumen catheter devices which are designed for enhancement of fluid flow through a vascular site that is at least partially, if not totally, occluded by a vascular lesion, particularly a vascular calcified lesion. The subject multi-lumen catheter devices comprise at least three distinct lumens, i.e. the subject devices at least include a first, second and third lumen.

The first lumen is characterized in that it has at least an inner wall that is resistant to reaction with an acidic dissolution fluid, at least for a period of time sufficient for the intended use of the catheter to be completed. More specifically, at least the inner wall of the catheter is fabricated from a material that is resistant to reaction with a solution having a pH of less than about 4, preferably less than about 2 and more preferably less than about 1. As such, it must be inert to a solution that has a pH from about 0 to 4. Generally, the material from which the inner surface of the first lumen is fabricated must be resistant to reaction with an acidic solution, e.g. must be substantially inert with respect to the acidic dissolution fluid, for a period of time that is at least about 10 min long, preferably at least about 20 min long and more preferably for at least about 1 hour long or longer. Materials of interest from which at least the inner surface of the first lumen may be fabricated include: biocompatible polymers, e.g. polyimide, PBAX[], polyethylene, and the like. The thickness of the inner surface of the first lumen must be sufficient to protect the remainder of the catheter device from any corrosive reaction with the acidic dissolution solution that is conveyed or delivered through the first lumen during use of the catheter device, as described in greater detail infra. As such, the thickness of the inner wall is typically at least about 0.5 mm, usually at least about 0.1 mm and more usually at least about 0.25 mm. The first lumen of the subject multi-lumen catheter devices is further characterized in that it is capable of being attached in fluid communication, either directly or indirectly, with an acidic dissolution fluid reservoir. The effective total cross sectional area through which acidic dissolution fluid flows during use of the subject devices, (i.e. the total cross-sectional areas of any openings present at the distal end of the first lumen less any area occupied by a blocking element positioned in any of the openings) is sufficient to provide the requisite rate of flushing of the vascular occlusion with the acidic dissolution fluid. Generally, the effective total cross sectional area provided by the at least one opening at the distal end of the first lumen is at least about 0.1 mm$^2$, often at least about 0.2 mm$^2$ and somtimes at least about 0.3 mm$^2$, where the total effective cross sectional area at the distal end of the first lumen may be as large as 0.6 mm$^2$ or larger, but in certain embodiments will not exceed about 0.5 mm$^2$ and in other embodiments will not exceed about 0.4 mm$^2$.

The second lumen of the subject catheter device is employed to convey or deliver a pH elevating fluid, e.g. a buffer, to a vascular site, as described in greater detail infra. As such, the second lumen of the subject multi-lumen catheter devices is characterized in that it is capable of being attached in fluid communication, either directly or indirectly, with a pH elevating fluid reservoir. The effective total cross-sectional area of the opening at the distal end of the second lumen, where effective total cross-sectional area is as defined above (e.g. the annular space in a coaxial embodiment, as described in greater detail infra), is sufficient to provide the requisite amount of pH elevating solution to the vascular site so that any portion of the vascular site apart from the target surface of the vascular solution is not contacted with a solution which has a pH of less than about 4, preferably less than about 5 and more preferably less than about 6. Accordingly, the effective cross-sectional area of the opening(s) of the distal end of the second lumen is at least about 0.8 mm$^2$, usually at least about 1.4 mm$^2$ and may be as larger as 2.2 mm$^2$ or larger, but generally does not exceed about 2.0 mm$^2$ and usually does not exceed about 1.5 mm$^2$.

The third lumen of the subject multi-lumen catheter devices is an aspiration lumen. The aspiration lumen is characterized by at least having a distal opening(s) with an effective total cross-sectional area (e.g. the area of the annular space in the coaxial embodiments described infra) that is sufficiently large to remove fluid, and debris, from the vascular site at substantially the same rate that fluid (e.g. buffer solution and acidic dissolution solution) is introduced into the vascular site during use of the device, such that the fluid pressure in the vascular site remains substantially isobaric or isometric, where by substantially isobaric or isometric is meant that the fluid pressure in the vascular site does not vary by more than about 50 mm Hg, preferably does not vary by more than about 10 mm Hg, and more preferably does not vary by more than about 5 mm Hg over the total flushing period.

The subject catheter devices are further characterized by at least including a first vascular occlusion means positioned at some point proximal to the distal end of the outer surface of the catheter device, e.g. the outer surface of the aspiration catheter in the coaxial embodiments described infra. By vascular occlusion means is meant any device or component that is capable of substantially, and preferably completely, occluding a vessel, e.g. an artery or vein. By substantially occluding is meant that fluid, e.g. blood, flow past the occlusion means upon activation is reduced by at least 95%, usually by at least 97% and more usually by at least 99%, where in preferred embodiments, fluid flow is reduced by 100% such that the fluid flow into the vascular site is substantially, if not completely, inhibited. Any convenient means may be employed, where a vascular occlusion means of particular interest includes an inflatable balloon. Inflatable balloons are well known in the catheter art, and any convenient balloon configuration may be employed. While the inflatable balloon may be one that is designed to be inflated with a gas or liquid, of particular interest in many embodiments are those that are configured to be inflated with a liquid, e.g. a pH elevating solution as described in greater detail infra.

Catheter Devices—Specific Alternative Embodiments

The subject invention provides a number of distinct alternative embodiments of the subject catheter devices. One preferred specific embodiment of interest is a coaxial embodiment, in which each of the first, second and third lumens are coaxial. Other alternative embodiments include embodiments in which at least one of the lumens is not coaxial with the other lumens, as well as embodiments in which none of the lumens is coaxial. Each of these representative alternative embodiments is now described in greater detail below.

Coaxial Embodiments

As mentioned above, a preferred embodiment of the subject multi-lumen catheter devices is a coaxial embodiment, in which the first, second and third lumens of the subject catheter device are coaxial. By "coaxial" is meant that the first, second and third lumens share a common axis. As such, in these embodiments the first lumen is present in an element positioned inside the second lumen, which in turn is present in an element positioned inside the third lumen. Generally, the first, second and third lumens are found inside fluid delivery means which are positioned inside one another, where the fluid delivery means are often elongated tubular elements. The coaxially positioned fluid delivery means comprising the first, second and third lumens, i.e. the first, second and third fluid delivery means, may be held in a static relationship with respect to one or another or may be movable with respect to one another, such that at least one of the fluid delivery means, and preferably at least two of the fluid delivery means may be moved without moving the other fluid delivery means—i.e. each of the first, second and third fluid delivery means may be moved independently of one another. Spacers or other means on the inner walls of at least the second and third lumens may be present to maintain the coaxial configuration.

In this coaxial embodiment of the subject invention, one of the lumens serves to deliver an acidic dissolution fluid, one of the lumens serves to deliver a pH elevating fluid and one of the lumens serves to remove fluid from the vascular site. In other words, two of the lumens serve to introduce fluid to the vascular site and one of the lumens serves to remove fluid from the vascular site. While any of the lumens may serve any of the above functions, generally, the first lumen which delivers the acidic dissolution solution (i.e the one that has at least an inner surface that is substantially inert to the acidic dissolution fluid) is the innermost lumen of the coaxial lumens of the device. As such, the first lumen is the lumen with the inner walls that are closest to the center line or axis of the coaxial catheter device.

The first lumen is generally positioned along the center line or axis of a first elongated fluid delivery means, where the fluid delivery means generally extends along the length of the catheter from its proximal to distal end. The fluid delivery means is typically tubular in shape, and may have a variety of different cross-sectional configurations, including square, triangular, trapezoidal, circular, elliptical, irregular, and the like, where often the cross-sectional shape of the elongated tubular member is curvilinear, and more often is circular.

The design of the first fluid delivery means may vary depending on the nature of the target vascular occlusion, e.g. whether the target vascular occlusion is a total occlusion or a partial occlusion. The total occlusion first fluid delivery means, e.g. the total occlusion catheter insert, is an elongated tubular structure, as described above, having a blunt ended, open distal end through which fluid may be flowed under pressure. The length of the total occlusion catheter insert generally ranges from about 90 to 210 cm, usually from about 100 to 190 cm and more usually from about 110 to 150 cm. The outer diameter of the total occlusion catheter insert is such that the catheter insert may be slidably positioned in the second lumen (i.e. the lumen of the second fluid delivery means, as described infra), and typically ranges from about 0.4 to 2.0, usually from about 0.4 to 1.6 mm. The inner diameter of the total occlusion catheter insert typically ranges from about 0.2 to 1.0, usually from about 0.25 to 1.0 and more usually from about 0.3 to 1.0 mm.

Where the target occlusion is a partial occlusion, a partial occlusion first fluid delivery means is employed, i.e. a partial occlusion catheter insert. The partial occlusion catheter insert differs from the total occlusion catheter insert in a number of ways. First, the partial occlusion catheter insert includes a balloon or analogous vessel occlusion means at its distal end, where the distance between the vascular occlusion means and the distal end of the catheter insert typically ranges from 1 to 30 mm, usually from about 10 to 20 mm. Second, the partial occlusion vascular insert has one or more fluid introduction ports proximal to the proximal side of the distal balloon. The diameter of the infusion ports may vary, but typically ranges from about 0.2 to 1.2, usually from about 0.4 to 1.0 and more usually from about 0.5 to 0.8 mm. Where the vascular occlusion means on the partial occlusion catheter insert is a balloon, a balloon inflation lumen is also present in the partial occlusion catheter insert. Finally, the end of the partial occlusion catheter insert is sealed. The length of the partial occlusion catheter insert generally ranges from about 90 to 250 cm, usually from about 100 to 230 cm and more usually from about 110 to 190 cm. The outer diameter of the partial occlusion catheter insert is such that the catheter insert may be slidably positioned in the second lumen, i.e. the lumen of the second fluid delivery means, as described infra. The outer diameter typically ranges from about 0.5 to 2.0. The inner diameter of the partial occlusion catheter insert typically ranges from about 0.2 to 1.0, usually from about 0.25 to 1.0 and more usually from about 0.3 to 1.0 mm.

Figure 2B:
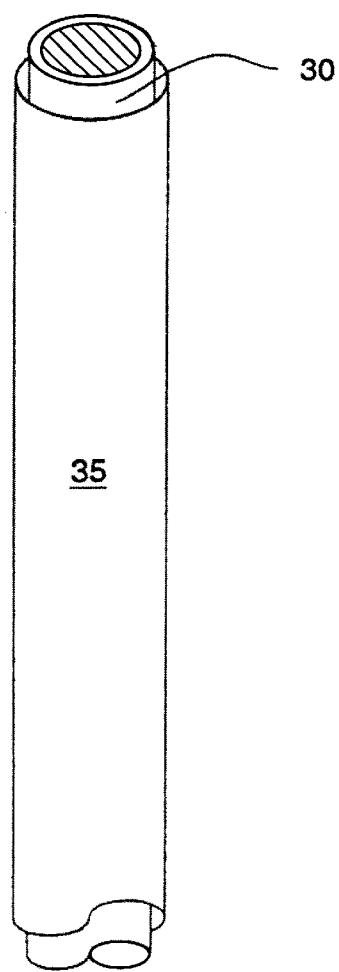
Figure 3:
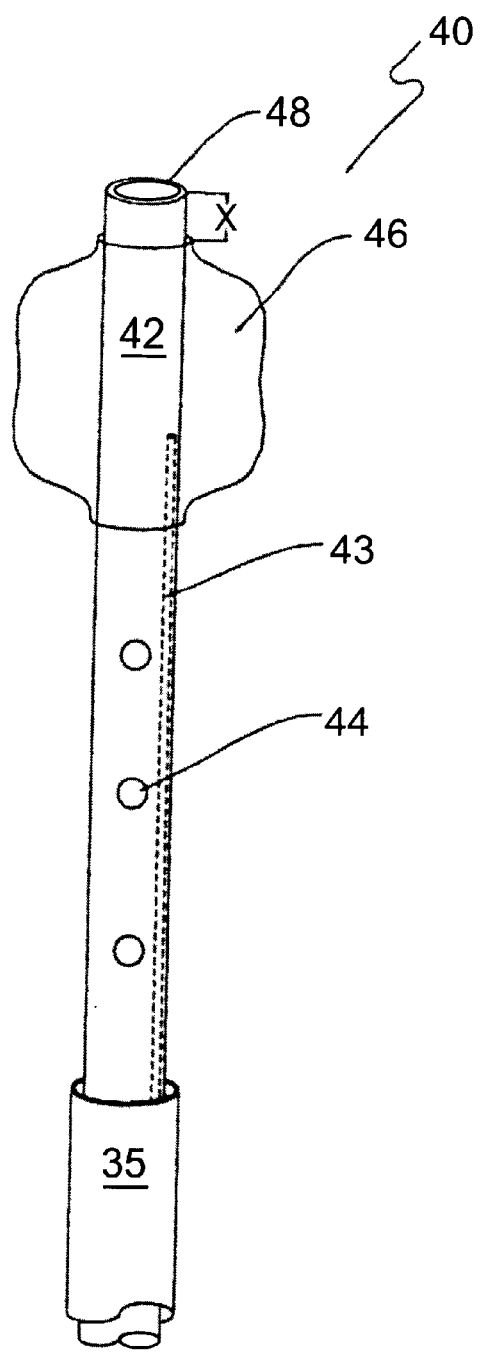
FIG. 3 provides a representation of a partial occlusion catheter insert for use in the aspiration catheter of FIG. 2A.

The above described partial and total catheter inserts are further characterized by being capable of being attached at their proximal ends, either directly or through one or more attachment means, to a fluid reservoir, e.g. an acidic dissolution fluid reservoir and, in the case of the partial occlusion catheter insert, a balloon inflation means. A representation of a total occlusion catheter insert 30 according to the subject invention is provided in FIG. 2B. A representative partial occlusion catheter insert is provided in FIG. 3. In FIG. 3, partial occlusion catheter insert 40 includes elongated tubular structure 42 that is sealed at its distal end 48. Proximal to the distal end 48 is balloon 46, where the distance Y typically ranges from about 1 to 30 mm, usually from about 10 to 20 mm. Also depicted are infusion ports 44. The diameter of the infusion ports may vary, but typically ranges from about 0.2 to 1.2, usually from about 0.4 to 1.0 and more usually from about 0.5 to 0.8 mm. Also shown is balloon inflation lumen 43, where the balloon inflation lumen has dimensions similar to those of balloon inflation lumen 23. As evidenced, the partial occlusion catheter insert includes two lumens, a fluid introduction lumen and a balloon inflation lumen. Also visible in FIGS. 2B and 3 is second delivery means 35 which includes the second lumen, described in greater detail below.

The second lumen of the subject multi-lumen catheter devices is designed for delivery of a pH elevating solution to the vascular site of the target occlusion. This lumen is generally present in a second fluid delivery means (element 35 in FIGS. 2B and 3), where the fluid delivery means is generally an elongated tubular structure analogous to the first fluid delivery means described supra. In the present coaxial embodiment, the dimensions of this second fluid delivery means, i.e. second catheter insert, are such that the first fluid delivery means or catheter insert described above (i.e. either the partial or total occlusion catheter insert) can fit inside this second fluid delivery means, i.e. can fit inside the lumen of the second fluid delivery means. A further limitation is that the first fluid delivery means must fit inside the second fluid delivery means in a manner such that an annular space is formed in the second lumen which is sufficient to convey the requisite amount of pH elevating fluid to the vascular site during use of the device. As such, the inner diameter of the second lumen exceeds the outer diameter of the first fluid delivery means by at least about 0.6 mm, sometimes at least about 0.9 mm and in certain embodiments at least about 1.2 mm. Accordingly, the inner diameter of the second fluid delivery means ranges from about 0.8 to 2.5, usually from about 0.9 to 1.9 and more usually from about 1.0 to 1.3 mm. The second fluid delivery means has an open distal end which, when positioned around the first fluid delivery means during use, forms an annular opening through which pH elevating fluid flows out of the second fluid delivery means and into the vascular site during use. The total effective cross-sectional area of the annular opening typically ranges from about 0.6 to 2.6, usually from about 0.8 to 1.9 and more usually from about 0.9 to 1.3 mm$^2$. The overall length of the second fluid delivery means typically ranges from about 90 to 210, usually from about 100 to 190 and more usually from about 110 to 150 cm. The second fluid delivery means is further characterized by having a means for connecting to a pH elevating fluid reservoir, either directly or indirectly, at its proximal end.

Figure 12:
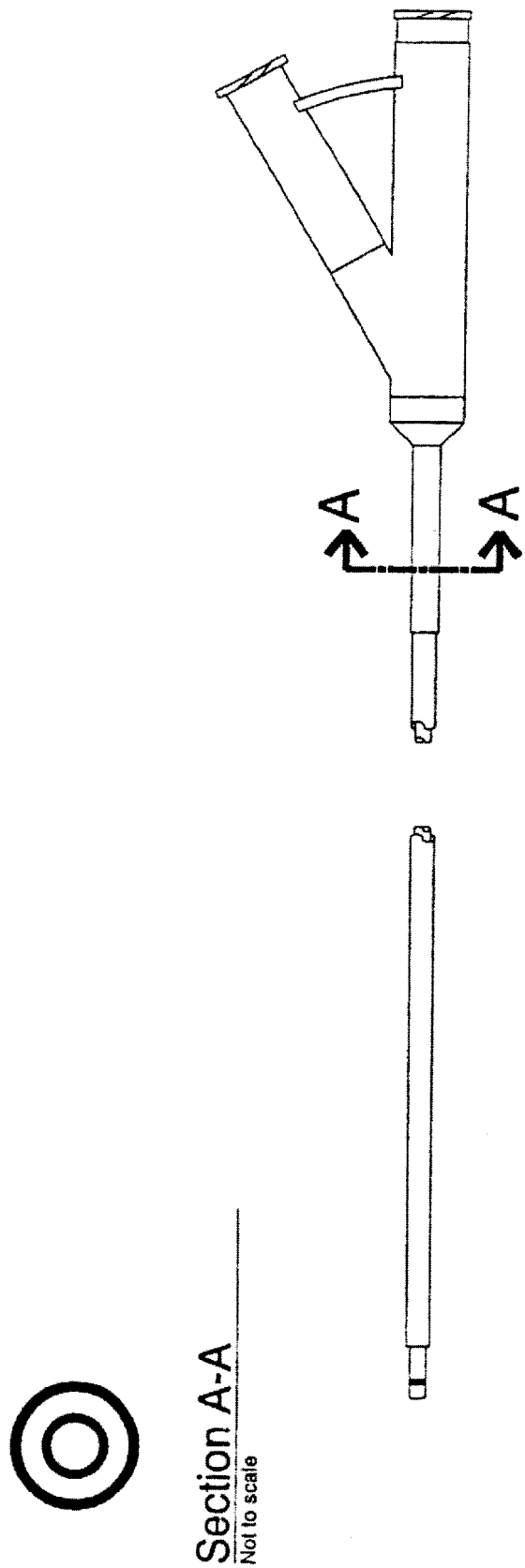
FIG. 12 provides another view of a total occlusion catheter of the catheter systems of the subject invention.

The first and second lumens and their respective fluid delivery means may be combined into integrated catheters in certain embodiments. An example of a total occlusion catheter unit is presented in FIG. 12 while an example of a partial occlusion catheter unit is presented in FIG. 13.

The third lumen in this coaxial embodiment of the subject devices is the outermost lumen, which is generally present in an elongated tubular structure analogous to the first and second fluid delivery means, as described above. The third lumen present in this third fluid delivery means is employed to remove fluid from the vascular site. As such, this third fluid delivery means is properly viewed as an aspiration catheter. The aspiration catheter is generally an elongated tubular structure fabricated from a flexible, biologically acceptable material having a balloon or analogous vessel occlusion means positioned at its distal end. The length of the aspiration catheter may vary, but is generally from about 80 to 200 cm, usually from about 90 to 180 cm and more usually from about 100 to 140 cm. The outer diameter of the aspiration catheter is selected so as to provide for access of the distal end of the catheter to the vascular site via the vascular system from the remote point of entry, where the outer diameter typically ranges from about 1.0 to 4.0 mm (3 to 12 Fr), usually from about 1.5 to 3.0 mm (4.5 to 9.0 Fr) and more usually from about 1.7 to 2.7 mm (5 to 8 Fr). The aspiration catheter is characterized by having an open distal end, where the inner diameter at the open distal end is sufficient to house the first and second coaxial fluid delivery means, as described supra, and remove fluid from the vascular site at the desired rate, e.g. a rate that provides for substantially isometric or isobaric pressure in the vascular site during treatment, through the resultant annular space. The inner diameter of the third or aspiration lumen, at least at its distal end and generally along the entire length of the aspiration catheter, typically ranges from about 0.2 to 2.0, usually from about 0.25 to 1.75 and more usually from about 0.35 to 1.5 mm. The total effective cross-sectional area at its distal end, i.e. the cross-sectional area of the annular space at the distal end opening, typically ranges from about 1.3 to 3.9, usually from about 1.3 to 3.2 and more usually from about 1.3 to 2.5 mm$^2$. Also present at the distal end of the aspiration catheter is a vessel occlusion means, where the vessel occlusion means is usually an inflatable balloon. The balloon is one that is inflatable to a volume sufficient to substantially occlude the vessel in which the aspiration catheter is positioned, e.g. by pressing against the intimal surface of the vessel in which the aspiration catheter is positioned. The balloon is in fluid or gaseous communication with an inflation lumen that runs the length of the aspiration catheter and can be connected to a balloon inflation means. The inflation lumen has an inner diameter that typically ranges from about 0.1 to 0.5, usually from about 0.2 to 0.4 mm. In certain embodiments, the aspiration catheter further includes a separate guidewire lumen. When present, the guidewire lumen has a diameter ranging from about 0.2 to 1.0 mm, usually from about 0.3 to 0.6 mm. Thus, the aspiration catheter includes at least two distinct lumens, i.e. an aspiration lumen (also referred to herein as the third lumen) and a balloon inflation lumen, and in many embodiments includes three distinct lumens, i.e. an aspiration lumen, a balloon inflation lumen and a guidewire lumen. A representation of an aspiration or irrigation catheter is provided in FIG. 14.

The aspiration catheter is further characterized by being capable of attaching, either directly or through one or more attachment means, at its proximal end to vacuum means, e.g. a negative pressure means, where such means is sufficient to provide for the desired aspiration during use of the device, and a balloon inflation means, where such means is sufficient to inflate the balloon at the distal end of the catheter when desired.

Figure 2A:
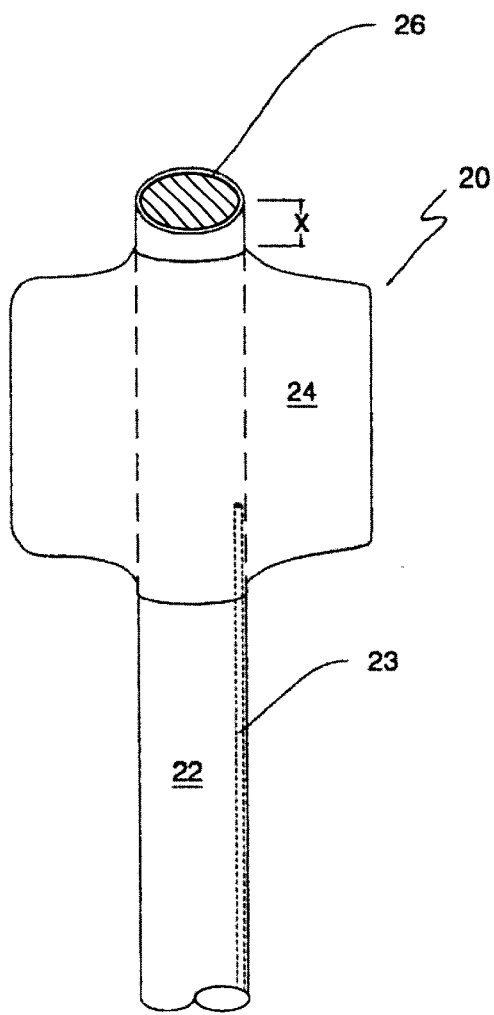
FIG. 2A provides a representation of an aspiration catheter according of an embodiment of the subject invention while FIG. 2B provides a representation of a total occlusion catheter insert for use in the aspiration catheter of FIG. 2A.

A representation of the aspiration catheter of the subject catheter systems found in the subject kits is provided in FIG. 2A. In FIG. 2A, aspiration catheter 20 includes elongated tubular member 22 and balloon 24 located proximal to the distal end. The distance X between the distal most portion of the balloon 24 and the distal end of the catheter typically ranges from about 1 to 20, usually from about 5 to 10 mm. Also shown is distal open end 26 through which either the partial or total occlusion insert catheter is moved and fluid is aspirated. Balloon 24 is inflatable via balloon inflation lumen 23.

Alternative Embodiments

In an alternative embodiments of the subject invention, at least two of the first, second and third lumens are not coaxial. In these alternative embodiments, the configuration of the first, second and third lumens in the device may vary greatly. For example, the first second and/or third lumens may be present on separate non-coaxial fluid delivery means. As such, the device could be made up of three different fluid delivery means bundled together to produce a triple lumen catheter device. Alternatively, a single fluid delivery means could house all three lumens. In certain embodiments, two of the lumens, i.e. the first and second lumen, will be present on a first fluid delivery means, which fluid delivery means is coaxially positioned within the third lumen. The first or internal fluid delivery means housing the first and second lumens may take on a variety of configurations. In one configuration, the first and second lumens terminate or open at the distal end of the internal fluid delivery means. In other configurations, one of the lumens opens at a different area from the other lumen. In these embodiments, the first lumen typically opens at the distal end of the internal fluid delivery means and the second lumen opens at a site proximal to the distal end of the internal fluid delivery means. The second lumen may open up at a one or more openings proximal to the distal end of the internal fluid delivery means. In each of these embodiments, the internal fluid delivery means housing the first and second lumens is present in a third lumen which is also housed by a fluid delivery means, where this fluid delivery means may be referred to as an aspiration catheter, as described above.

Catheter Systems

As summarized above, the subject invention also provides catheter systems suitable for use in the subject methods, as described in greater detail infra. By catheter system is meant two more disparate catheter components which are capable of being assembled into a single unit, i.e. coaxial catheter assembly, having at least an inner catheter that is slidably positioned within the lumen of an outer catheter, i.e. a coaxial catheter assembly having an inner insert catheter that can be moved relative to the outer catheter so as to produce varying distances between the distal ends of the two coaxial catheters. For example, a catheter system which includes the above described coaxial embodiments where all three first, second and third lumens are coaxial, will include disparate catheter fluid delivery means that fit within one another to produce a coaxial triple lumen catheter as described above. In such systems, the system will at least include an aspiration catheter, a pH elevating fluid delivery catheter and at least one internal fluid delivery catheter. In many systems according to this embodiment, the system will further include a second internal catheter, such that the first internal catheter is suitable for use in treating total occlusions and the second internal catheter is suitable for use in treating partial occlusions. An exemplary catheter system of the subject invention includes the partial occlusion catheter unit, the total occlusion catheter unit and the irrigation or aspiration catheter unit depicted in FIGS. 12 to 14.

Further Catheter Device and System Characteristics

The components of the subject catheter systems and catheter devices, as described above, may be fabricated from any convenient material, with the only limitation being that at least the inner surface of the first lumen be fabricated from a material that withstands, i.e. does not degrade upon contact with, the acidic dissolution fluid, at least for the period of time during which the catheter system is used. The materials must also be able to withstand the effects of any reaction byproducts produced by contact of the acidic dissolution solution with the components of the target occlusion. Suitable materials include biocompatible polymers, e.g. polyimide, PBAX[], polyethylene, and the like. Any glues or fittings that are employed must also be able to meet the same criteria. Any convenient fabrication protocol may be employed, where numerous suitable protocols are known to those of skill in the art.

Methods

Also provided by the subject invention are methods of locally introducing active agents to vascular sites. In the broadest sense, the subject catheter systems may be employed to introduce any active agent in a fluid delivery vehicle to a vascular site. The subject systems achieve local delivery of active agents in fluid delivery vehicles by irrigating or flushing a portion of the vascular system with the fluid agent composition. Active agents of interest that may be locally introduced using the subject methods include: thrombolytic agents, growth factors, cytokines, nucleic acids (e.g. gene therapy agents), detergents and surfactants, and the like. Of particular interest is the use of the subject catheter systems in the treatment of vascular calcified occlusions, which application will now be described in greater detail as representative of the various methods in which the subject catheter systems may be introduced.

For treatment of vascular calcified occlusions with the subject catheter devices and systems, the subject catheter systems are used to flush a surface of the target vascular occlusion with an acidic dissolution fluid for a period of time sufficient for fluid flow to be to be enhanced through the vascular site. As indicated above, by enhanced is meant that fluid flow is either established in situations where fluid flow is not initially present, e.g. where the target vascular occlusion is a total occlusion, or increased where some fluid flow through the vascular site is present, e.g. in situations where the vascular site is occupied by a partial occlusion. The subject methods are further characterized in that, simultaneously with the acidic dissolution fluid, a pH elevating fluid is also introduced into the vascular site of the target lesion, i.e. the target vascular site. A critical feature of the subject methods is that the subject devices are used to introduce both acidic dissolution fluid and pH elevating fluid to the target vascular site in a manner such that the acidic dissolution fluid primarily contacts the surface of the target occlusion, with the remainder of the target vascular site being contacted with fluid that has a pH which is much higher than that of the acidic dissolution fluid.

The Target Vascular Site

The target site through which fluid flow is enhanced by the subject methods is a site within a vessel, typically an artery or vein, and usually an artery. In many embodiments, the vascular site is a peripheral vascular site, by which is meant that the vessel in which the vascular site is located is a vessel found in one of the extremities of the patient to be treated, i.e. the arms or legs. Often, the vascular site is a site in a lower extremity vessel, e.g. a lower extremity artery. As indicated above, of particular interest in certain embodiments are peripheral arterial vascular sites, where specific peripheral arteries of interest include: iliac arteries, femoropopliteal arteries, infrapopliteal arteries, femoral arteries, superficial femoral arteries, popliteal arteries, and the like. In yet other embodiments, the vascular site is present in a heart associated vessel, e.g. the aorta, a coronary artery or branch vessel thereof, etc. In yet other embodiments, the vascular site is present in a carotid artery or a branch vessel thereof.

Figure 1B:
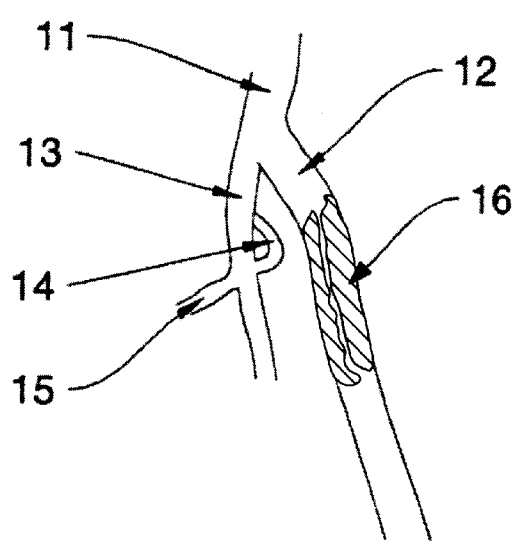

The vascular site is occupied by a vascular occlusion in such a manner that fluid flow through the vascular site, e.g. blood flow, is at least impeded if not substantially inhibited. By at least impeded is meant that fluid flow is reduced by at least 20%, usually by at least 50% and more usually by at least 80% through the vascular site as compared to a control. In such situations, the vascular site is occupied by a partial vascular calcified occlusion. By substantially inhibited is meant that substantially no fluid flows through the vascular site. For purposes of this invention, fluid flow through a vascular site is considered to be substantially inhibited where it is not possible to pass a guidewire through the vascular site, where the guidewire has a diameter ranging from 0.014 to 0.038 in and is applied to the site with a pressure ranging from about 1 to 30 oz. A representation of a peripheral artery having a vascular site occupied by a total vascular calcified occlusion is provided in FIG. 1A while a representation of a peripheral artery having a vascular site occupied by a partial vascular calcified occlusion is provided in FIG. 1B. In FIGS. 1A & 1B, the external iliac artery 11 is shown as it branches into the SFA 12 and the profunda 13. Also shown are the medial circumflex and the later circumflex, 14 and 15 respectively. The SFA is totally occluded by occlusion 16 in FIG. 1A and partially occluded by occlusion 16 in FIG. 1B.

The Target Vascular Occlusion

The vascular occlusion that occupies the target vascular site is generally a calcified vascular occlusion, by which is meant that the occlusion includes at least some calcium containing component. The calcified occlusion may be a substantially pure mineral structure, or may be a more complex formation that includes both mineral and other components, including organic matter, e.g. lipids, proteins, and the like. As mentioned above, the target vascular occlusion may be a partial or total vascular occlusion.

The mineral component making up the calcified lesion is generally made up of one or more calcium phosphates, where the calcium phosphates are generally apatitic. The term "apatite" as used herein refers to a group of phosphate minerals that includes ten mineral species and has the general formula $X_5(YO_4)_3Z$, where X is usually $Ca^{2+}$ or $Pb^{3+}$, Y is $P^{5+}$ or $As^{5+}$, and Z is $F^-$, $Cl^-$, or $OH^-$. The term calcium apatite refers to a group of phosphate minerals where X is $Ca^{2+}$. The mineral component of the calcified occlusion typically includes one or more of hydroxyapatite, carbonated hydroxyapatite (dahllite) and calcium deficient hydroxyapatite.

In addition to the mineral component, the calcified occlusion that occupies the target vascular site may also comprise one or more additional components, where such components include: lipids; lipoproteins; proteins; including fibrinogen, collagen, elastin and the like; proteoglycans, such as chondroitin sulfate, heparin sulfate, dermatans, etc.; and cells, including smooth muscle cells, epithelial cells, macrophages and lymphocytes. As such, calcified occlusions that are targets of the subject methods include those that may be described as: type IV, type V and type VI lesions, as defined in Stary et al., Arterioscler. Thromb. Vasc. Biol. (1995) 15:1512–1531.

In the vascular occlusions that occupy the target vascular sites of the subject methods, the mineral component of the calcified occlusion generally makes up from about 10 to 100, usually from about 10 to 90 and more usually from about 10 to 85 dry weight % of the occlusion. The size of the occlusion that is the target of the subject methods varies depending on location and specific nature of the occlusion. Generally, the volume of the occlusion will range from about 20 to 10,000 $mm^2$, usually from about 30 to 500 $mm^3$ and more usually from about 50 to 300 $mm^3$.

In certain embodiments, one or both ends of the occlusion may be characterized by being primarily thrombotic material, e.g. a thrombus, where the thrombotic domain of the occlusion extends for about 1 to 5 cm. The nature of the thrombotic domain may be organized or disorganized.

Contacting the Vascular Occlusion with an Acidic Dissolution Fluid

In the subject methods, one surface of the vascular occlusion, e.g. the distal or proximal surface, is contacted with an acidic dissolution fluid for a period of time sufficient for fluid flow to be established or enhanced through the vascular site. Contact with the vascular site may be accomplished in any convenient manner, so long as it results in the enhancement of fluid flow through the vascular site. Generally, the surface is dynamically contacted or flushed with the acidic dissolution fluid.

By dynamic contact is meant that the fresh dissolution solution is contacted with the surface of the target occlusion one or more times, including continuously, during the treatment period. In many preferred embodiments of the subject methods, the surface of the target occlusion is continuously contacted or flushed with the acidic dissolution fluid. In other words, the acidic dissolution fluid is introduced in a manner such that a continuous flow of the acidic dissolution fluid across the surface of the occlusion is achieved.

Where the surface of the target occlusion is flushed with the dissolution fluid, it is preferred that the pressure in the local environment which includes the surface of the occlusion, i.e. the area bounded by the vessel walls, the surface of the target occlusion and the catheter system used to deliver the solution, remains substantially isometric. By substantially isometric is meant that the pressure in the local environment does not vary by a significant amount, where the amount of variance over the treatment period does not vary by more than about 50%, usually by not more than about 10% and more usually by not more than about 5%. In other words, the local environment remains substantially isobaric during the treatment period. Accordingly, where fluid is dynamically contacted with the surface of the target occlusion, fluid is also simultaneously removed from the local environment comprising the surface of the target occlusion, such that the overall volume of fluid in the local environment remains substantially constant, where any difference in volume at any two given times during the treatment period does not exceed about 50%, and usually does not exceed about 10%. As such, the dissolution fluid is introduced into the local environment of the target lesion in a manner such that the local environment remains substantially isovolumetric.

Where the acidic dissolution fluid is dynamically introduced into the vascular site, the dissolution fluid is introduced in a manner such that the flow rate of the dissolution solution through the vascular site of the lesion is generally at least about 10 cc/min, usually at least about 20 cc/min and more usually at least about 60 cc/min, where the flow rate may be as great as 120 cc/min or greater, but usually does not exceed about 1000 cc/minute and more usually does not exceed about 500 cc/minute, where by [volume] is meant the local environment of the occlusion, as defined above. The total amount of dissolution fluid that is passed through the local environment of the lesion during the treatment period typically ranges from about 100 to 1000 cc, usually from about 200 to 800 cc and more usually from about 400 to 500 cc. The solution is generally pressurized to achieve the desired flow rate, as described supra. As such, the pressure at the distal end of the coaxial catheter assembly through which the solution is introduced into the local environment typically ranges from about 50 to 1200 psi, usually from about 100 to 600 psi and more usually from about 200 to 400 psi. It is important to note that the overall pressure in the local environment is maintained at substantially isometric or isobaric conditions. As such, the negative pressure at the entrance to the aspiration catheter, e.g. the open annulus at the distal end of the aspiration catheter will be of sufficient magnitude to provide for substantially isobaric conditions. Preferably, the overall pressure in the local environment is maintained at a value ranging from about 0.1 to 3 psi, usually from a bout 0.5 to 2.5 psi and more usually from about 1 to 2 psi.

As indicated above, a critical feature of the subject methods is that the target vascular site is flushed with a pH elevating solution concomitantly or simultaneously with the acidic dissolution fluid in a manner sufficient such that only the surface of the target occlusion, and not the remainder of the target vascular site, is contacted with a low pH solution. By pH elevating solution is meant any solution that, upon combination with the acidic dissolution solution, produces a solution with an elevated pH with respect to the acidic dissolution solution. In principle, any fluid that, upon combination of with the acid dissolution fluid produces a solution having a pH higher than that of the acidic dissolution fluid, may be employed, so long as the fluid is biocompatible, at least for the period of time that it is present in the target vascular site. The pH elevating solution should have a pH of at least about 4, usually at least about 6 and more usually at least about 8. As such, pH elevating fluids of interest include water, physiological acceptable buffer solutions, etc., where in many embodiments, the pH elevating solution is a buffer solution. Representative buffer solutions of interest include: phosphate buffered saline, sodium bicarbonate and the like.

In the subject methods, the acidic dissolution and pH elevating fluids are introduced into the vascular site in a manner such that only the target vascular lesion is contacted with the low pH acidic dissolution fluid. As such, the remainder of the target vascular site is contacted with a fluid that has a pH well above that of the acidic dissolution fluid, where the lowest pH to which the remainder of the target vascular site is subjected to is not less than 4, preferably not less than 5 and more preferably not less than 6. In other words, only the target vascular occlusion is contacted with the low pH acid dissolution fluid while the remainder of the target vascular site is contacted with a solution the pH of which is not less than 4, preferably not less than 5 and more preferable not less than 6. A representation of a target vascular site being flushed with both an acidic dissolution fluid and a pH elevating fluid according to the subject methods is provided in FIGS. 4, 6 and 11.

Figure 4:
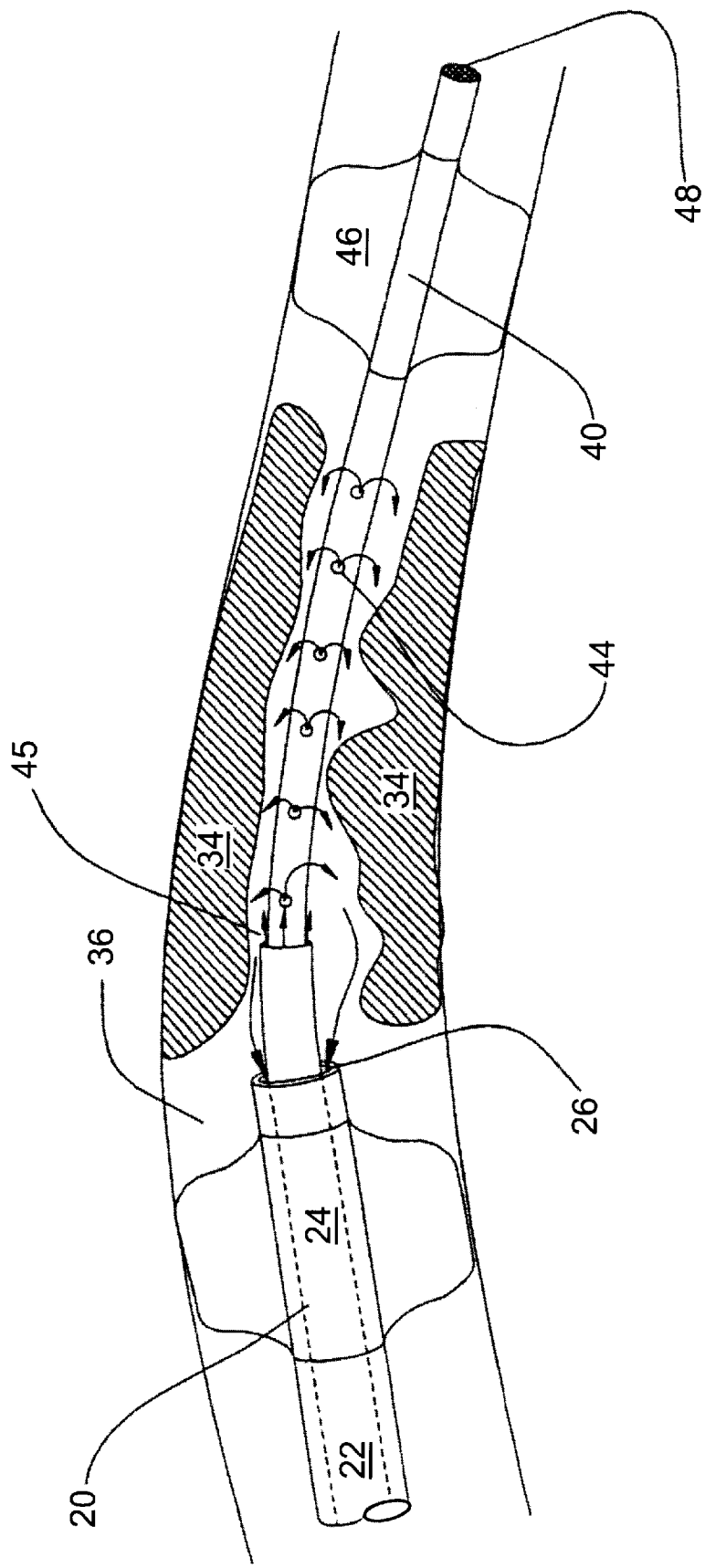
FIG. 4 provides a depiction of the use of the partial occlusion catheter system according to the subject invention.
Figure 6:
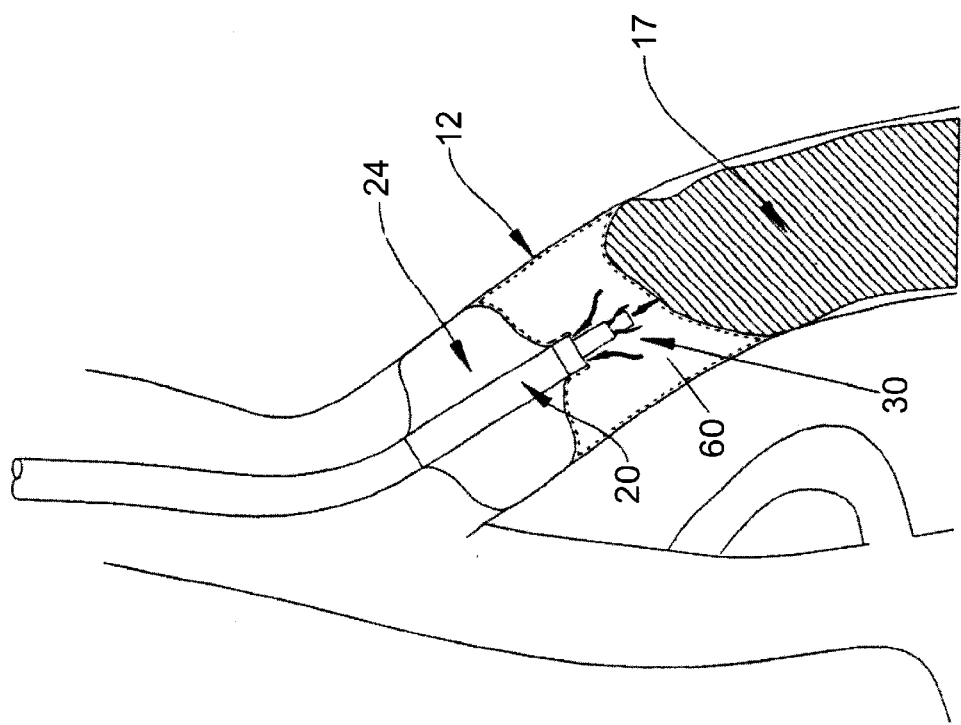
Figure 11:
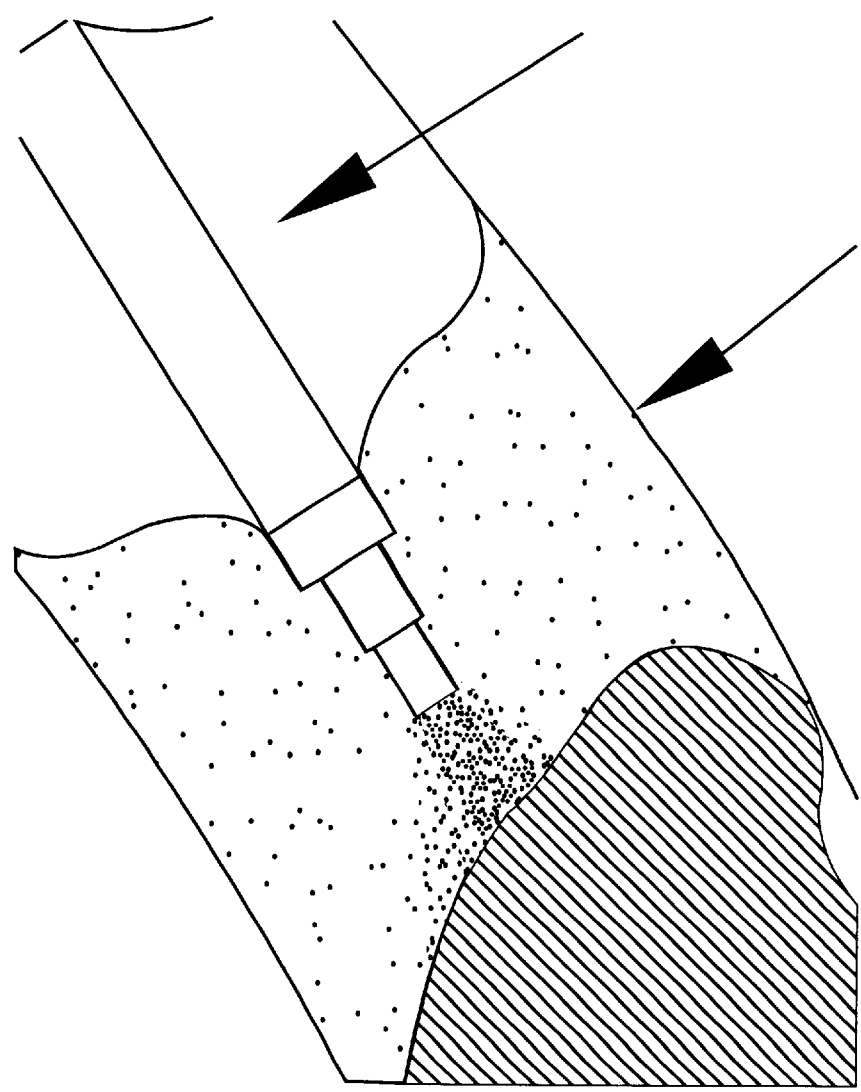
FIG. 11 illustrates the limited range of the acidic dissolution fluid when applied according to the subject methods.

In FIG. 4, where the target lesion is a partial occlusion, a coaxial partial occlusion catheter device, as described above, is introduced into the vascular site such that the balloon 46 of the partial occlusion insert 40 and the balloon 24 of the aspiration catheter 20 flank the partial occlusion 34. Acidic dissolution fluid is introduced by the plurality of ports 44 on the partial occlusion insert. A pH elevating solution is concomitantly introduced through annular space 45. Fluid is then removed from the vascular site by the aspiration catheter 20 through annular space 26. FIG. 6 provides a view of a total occlusion catheter insert flushing a vascular site 12 of a total occlusion 17. As can be seen in FIG. 6, acidic dissolution fluid is introduced through the central catheter and pH elevating solution is introduce via the catheter immediately concentric with the center catheter. Fluid is removed from the vascular site via the aspiration catheter, in which the central and intermediate catheters are coaxially positioned. FIG. 11 provides a representation of the pH gradients which occur in the vascular site during treatment according to the present invention. The darkest area represents the lowest pH. The grey area represents the highest pH, where the pH of this area is not lower than 4, usually not lower than 5 and preferably no lower than 6.

Time Period

The surface of the target occlusion is contacted, e.g. flushed, with the acidic dissolution fluid for a period of time sufficient for fluid flow to be enhanced or established through the vascular site, e.g. established or improved. As such, where the target occlusion is a total occlusion, contact is maintained for a period of time sufficient for a guidewire to be passed through the vascular site, as described above. Alternatively, where the target occlusion is a partial occlusion, contact is achieved for a period of time sufficient for the rate of fluid flow to be increased through the vascular site, generally by at least about 10%, usually by at least about 50%, and in many embodiments by at least about 100%. Generally, the period of time during which the surface of the occlusion is contacted with the acidic dissolution solution ranges from about 5 to 100 minutes, usually from about 10 to 30 minutes. Where contact is achieved by flushing the target occlusion with the acidic dissolution solution, the contact duration typically lasts for a period of time ranging from about 5 to 30 minutes, usually from about 10 to 30 minutes and more usually from about 10 to 20 minutes.

Acidic Dissolution Solutions

A variety of different types of acidic dissolution solutions may be employed in the subject methods. The acidic treatment solutions that find use in the subject methods generally have a pH of less than about 6.5, where the pH is usually less than about 4.0 and more usually less than about 3.0. In many preferred embodiments, the pH ranges from 0 to 2, and usually 0 to 1. The acidic treatment solution can include a number of different types of acids, where the acids may or may not include a hydrocarbon moiety, i.e. a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiotic acids. For such acids, the acid can be a concentrated acid, or can be diluted. Upon dilution, the concentration of an inorganic acid will generally be from about 10 N to about 0.01 N, preferably between 5 N to 0.1 N. Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form, or can be diluted. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

In many embodiments of the subject invention, the acid solution is hypertonic, by which is meant that the osmolarity of the solution is greater than that of whole blood, i.e. the osomolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of a hydrogen chloride solution. In hydrogen chloride solutions that find use in the subject invention, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Of particular interest are aqueous hydrogen chloride solutions that consist of water, hydrogen chloride and NaCl. The concentration of hydrogen chloride in these solutions of particular interest ranges from about 0.01 to 1.0 N, usually from about 0.05 to 0.5 N and more usually from about 0.075 to 0.25 N. The concentration of NaCl in these solutions of particular interest ranges from about 0.05 to 0.25 M, usually from about 0.05 to 0.10 M.

Further Embodiments of the Subject Methods

In a number of embodiments of the subject methods, the methods in which the surface of the target occlusion is contacted with an acidic dissolution fluid may be modified to include a number of additional method steps. Additional method steps that may be present in the overall process include: rendering the local environment of the target occlusion bloodless, contacting the target occlusion with a solution designed to remove organic components, washing or rinsing the local environment of the target occlusion, applying external energy to the target occlusion; imaging the target vascular site; establishing or expanding a passageway through an initial thrombotic domain of the target occlusion; and the like.

Rendering the Local Environment Bloodless In many preferred embodiments, as described above, the local environment of the target occlusion is rendered substantially bloodless prior to introduction of the acidic dissolution fluid. In these embodiments, the balloon(s) of the assembled catheter system is inflated to physically isolate the local environment from the remainder of the circulatory system and then the local environment is flushed with a physiologically acceptable solution, such that substantially all of the blood present in the solution is removed. Typically, a washing solution will be employed in this step of rendering the local environment bloodless. Examples of washing solutions that may find use in these embodiments include: water for injection, saline solutions, e.g. Ringer's, phosphate buffered saline, or other physiologically acceptable solutions. The washing solution includes an anticlotting factor in many embodiments, where anticlotting factors of interest include heparin and the like. The washing solution can also contain chelating agents.

Use of Organic Structure Dissolution Solutions

As mentioned above, in addition to the acidic dissolution solution, certain embodiments of the subject invention include a step of contacting the target occlusion with a dissolution solution which serves to remove at least a portion of the non-mineral, typically organic, phase of the target occlusion. The nature of this 'organic phase dissolution solution' varies depending on the nature of the target occlusion. Representative active agents that may be present in this organic phase dissolution solution include: oxidizing agents; organic solvents; lipid dissolving agents such as surfactants, e.g. TWEEN™, and detergents, where ionic detergents are of particular interest, e.g. cholic acid, glycocholic acid, benzylkonium chloride; enzymes, and the like.

Application of External Energy

In certain embodiments, external energy is applied to the vascular site to promote mechanical break-up of the occlusion into particles or debris that can be easily removed from the vascular site. Any means of applying external energy to the vascular site may be employed. As such, jets or other such means on a catheter device which are capable of providing varying external forces to the occlusion sufficient to cause the occlusion to break up or disrupt may be employed. Of particular interest in many embodiments is the use of ultrasound. The ultrasound can be applied during the entire time of contact of the cardiovascular tissue with the acidic treatment solution, or the ultrasound can be applied for only part of the treatment period. In one embodiment, ultrasound is applied for several short periods of time while the dissolution treatment solution is contacted with the target occlusion. There are several devices for the application of ultrasound to cardiovascular tissue known to those of skill in the art. See e.g. U.S. Pat. No. 4,808,153 and U.S. Pat. No. 5,432,663, the disclosures of which are herein incorporated by reference.

In such methods where external energy is applied to the occlusion in order to disrupt or break-up the occlusion into particles or debris, the particles or debris may range in size from about 0.01 to 4.0 mm, usually from about 0.1 to 2.0 mm and more usually from about 0.5 to 1.0 mm. In such instances, the method may further include a step in which the resultant particles are removed from the vascular site. Particles may be removed from the vascular site using any convenient means, such as the catheter of the subject invention described in greater detail infra.

Another means that may be employed to apply external energy to the lesion during the dissolution process is to use a mechanical means of applying external energy. Mechanical means of interest include moving structures, e.g. rotating wires, guidewires, which physically contact the target occlusion and thereby apply physical external energy to the target lesion. See e.g. FIGS. 9 and 10.

Imaging

In addition, it may be convenient to monitor or visualize the vascular site prior to or during treatment. A variety of suitable monitoring means are known to those of skill in the art. Any convenient means of invasive or noninvasive detection and/or quantification may be employed. Such means include plain film roentgenography, coronary arteriography, fluoroscopy, including digital subtraction fluoroscopy, cinefluorography, conventional, helical and electron beam computed tomography, intravascular ultrasound (IVUS), magnetic resonance imaging, transthoracic and transesophageal echocardiography, rapid CT scanning, antioscopy and the like. Any of these means can be used to monitor the vascular site before, during or after contact with the dissolution fluid.

In many embodiments, an imaging agent is employed, where the imaging agent may or may not be present in the acidic dissolution solution. Imaging agents of particular interest include: non-ionic imaging agents, e.g. CONRAY™, OXILAN™, and the like.

Thrombus Removal Step

The subject methods may further include a thrombus removal step, e.g. where the calcified domain of the target occlusion is covered by a thrombotic domain, as described above. In such methods, any thrombus removal means that is capable of providing sufficient access of the acidic dissolution solution to the surface the calcified domain of the target lesion may be employed. Thus, where the thrombotic domain is a disorganized domain, it may be sufficient to pass increasingly larger diameter guidewires through the domain until a passageway of sufficient width to provide access of the catheter assembly described above to the surface of the occlusion is established. Alternatively, portions of the thrombotic domain may be removed, e.g. via atherectomy methods, angioplasty methods, and the like, where devices for performing such procedures are known to those of skill in the art. See the patent references cited in the Relevant Literature section, supra, which references are herein incorporated by reference.

Use of a Plurality of Solutions

In many embodiments, the subject methods include contacting the surface of the target occlusion with a plurality, i.e. two or more, distinct solutions, one of which is an acidic dissolution solution. Where one or more additional distinct solutions, such as priming solutions, washing solutions, organic phase dissolution solutions and the like are employed, as described below, such disparate solutions are generally introduced sequentially to the vascular site. For example, the target occlusion may be contacted with the following order of solutions: (1) washing solution to render the local environment substantially bloodless; (2) organic phase dissolution solution, e.g. detergent solution such as cholic acid solution, to remove organic phases from the target lesion; (3) acidic dissolution solution to demineralize the target occlusion; and (4) washing solution. Other sequences of solution application can also be employed. See U.S. patent application Ser. No. 09/353,127, the disclosure of which is herein incorporated by reference. Generally, in any method where a plurality of different solutions are contacted with the target occlusion, a pH elevating solution is introduced simultaneously with at least the acidic dissolution solution, as described above.

Outcome

As discussed above, the subject methods result in the enhancement of fluid flow through the vascular site occupied by the occlusion. Fluid flow is considered to be enhanced in those situations where the vascular site is totally occluded when a guide wire can be moved through the vascular site without significant resistance. Fluid flow is considered to be enhanced in those situations in which the vascular site is partially occluded when the rate of fluid flow through the vascular site increases by at least 10%, usually by at least 50% and in many embodiments by at least 100%.

In certain embodiments, the subject methods will not result in complete removal of the target occlusion from the vascular site. As such, the vascular site, while not totally occluded, may still include lesion deposits on the wall which impede fluid flow through the vascular site and the removal or reduction of which is desired. Any convenient protocol for treating these remaining deposits may be employed, e.g. balloon angioplasty, atherectomy, stenting, etc. Also of interest is the use of two balloon catheters and an acidic dissolution solution, as described in PCT/US99/15918, the disclosure of which is herein incorporated by reference.

Of particular interest in those embodiments where the vascular site is initially totally occluded, fluid flow through the total occlusion is first established using the catheter assembly made up of the total occlusion catheter insert inside the aspiration catheter. Following establishment of fluid flow, the rate of fluid flow is increased using the catheter assembly made up of the partial occlusion catheter insert inside the aspiration catheter.

Additional Applications

In addition to methods of enhancing fluid flow through a target vascular site, methods and devices are also provided for reducing the mineral content of non-intimal tissue, as described in copending application Ser. No. 09/382,571, the disclosure of which is herein incorporated by reference. Specifically, the subject invention provides methods and devices that are analogous to those disclosed in the copending application, with the only difference being that the target tissue is contacted simultaneously with both the acidic dissolution solution and a pH elevating solution. As such, the devices are modified such that a means for introducing a pH elevating solution at the same time as the acidic dissolution solution to the target tissue is provided.

Systems

Also provided by the subject invention are systems for practicing the subject methods, i.e. for enhancing fluid flow through a vascular site occupied by a vascular occlusion. The subject systems at least include the catheter systems as described above, a manifold, a fluid reservoir for storing acidic dissolution fluid, a fluid reservoir for storing a pH elevating fluid and a negative pressure means for providing aspiration or suction during use of the system. The systems may further include a number of optional components, e.g. guidewires, pumps for pressurizing the dissolution fluid, and the like. See e.g. U.S. patent application Ser. No. 09/384,860, the disclosure of which is herein incorporated by reference.

Figure 5:
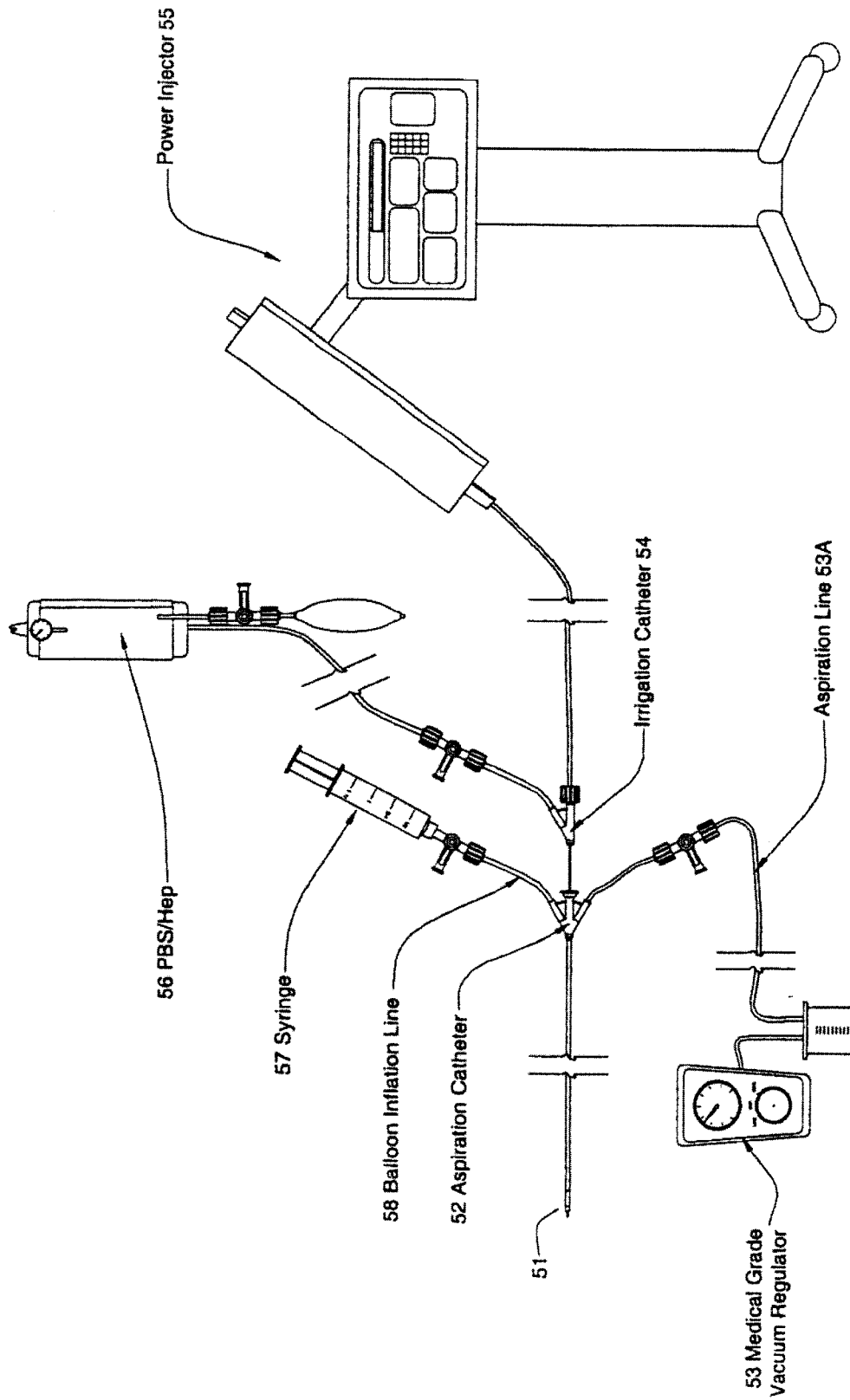
FIG. 5 provides a representation of a system according to the subject invention, which system includes a catheter device, manifold, fluid reservoirs, etc.

A representative system is provided in FIG. 5. In FIG. 5, system 50 is characterized by having catheter device 51 in fluid communication with the various fluid and vacuum sources require to practice the methods as described above. Specifically, the outer aspiration catheter 52 of the catheter device 51 is in communication with a medical grad vacuum regulator and vacuum means 53 by aspiration line 53A. The central or irrigation catheter 54 of the catheter device 51 is in fluid communication with power injector source of acidic dissolution solution, 55. The intermediate catheter of the catheter device 51 is in fluid communication with a source of pH elevating solution 56, e.g. PBS/Hep. Finally, syringe 57 is used to inflate the balloon of the catheter device via the balloon inflation line 58.

Utility

The subject devices and methods find use in a variety of different applications in which it is desired to enhance fluid flow, usually blood flow, (or at least pass a guidewire through), a vascular site that is occupied by a calcified vascular occlusion, e.g. a partial or total occlusion. As such, the subject methods and devices find use in the treatment of peripheral vascular disease, etc. The subject methods also find use in the treatment of coronary vascular diseases. By treatment is meant that a guidewire can at least be passed through the vascular site under conditions which, prior to treatment, it could not. Treatment also includes situations where the subject methods provide for larger fluid passageways through the vascular site, including those situations where fluid flow is returned to substantially the normal rate through the vascular site. The subject methods may be used in conjunction with other methods, including balloon angioplasty, atherectomy, and the like, as part of a total treatment protocol.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In many embodiments, the hosts will be humans.

Kits

Also provided by the subject invention are kits for use in enhancing fluid flow through a vascular site occupied by an occlusion. The subject kits at least include a catheter device or system, as described above. The kits may further include one or more additional components and accessories for use with the subject catheter systems, including tubing for connecting the various catheter components with fluid reservoirs, syringes, pumping means, etc., connectors, one or more guidewires, dilators, vacuum regulators, etc.

In certain embodiments, the kits further include one or more solutions, or precursors thereof, where in such embodiments the kits at least include an acidic dissolution fluid, such as a hydrochloric acid solution, as described above, where the solution may be present in a container(s), e.g. a flexible bag, a rigid bottle, etc. For kits that are to be used in methodologies in which the fluid is flushed through the local environment of the lesion, the amount of dissolution fluid present in the kit ranges from about 0.5 to 500 liters, usually from about 0.5 to 200 liters and more usually from about 0.5 to 100 liters. In many embodiments, the amount of dissolution fluid in the kit ranges from 0.5 to 5 liters, usually from about 0.5 to 2.0 liters and more usually from about 0.5 to 1.5 liters. Alternatively, the kit may comprise precursors of the dissolution solution for use in preparing the solution at the time of use. For example, the precursors may be provided in dry form for mixing with a fluid, e.g. water, at the time of use. In addition to the dissolution fluid or precursors thereof, the kit may further comprise one or more additional fluids (or dry precursors thereof), such as a priming solution, a washing solution, contrast medium, and the like. In many embodiments, the kits further include at least a pH elevating solution, e.g. a buffer solution such as phosphate buffered saline.

Other elements that may be present in the subject kits include various components of the systems, including manifolds, balloon inflation means, e.g. syringes, pumping means, negative pressure means etc.

Finally, the kits include instructions for practicing the subject methods, where such instructions may be present on one or more of the kit components, the kit packaging and/or a kit package insert.

The following examples are offered by way of illustration and not by way of limitation.

Experimental

Figure 7:
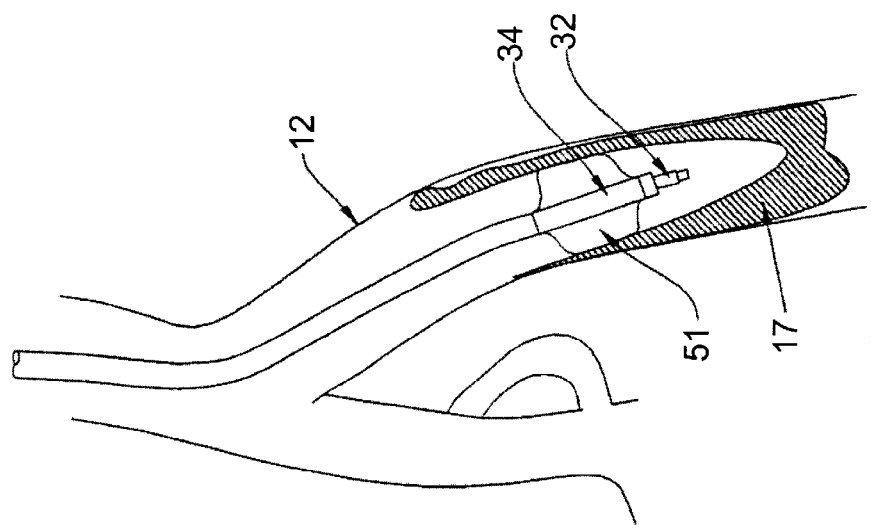
FIGS. 6 to 8 provides a representation of the various stages of the use of the total occlusion system of the subject invention.
Figure 8:
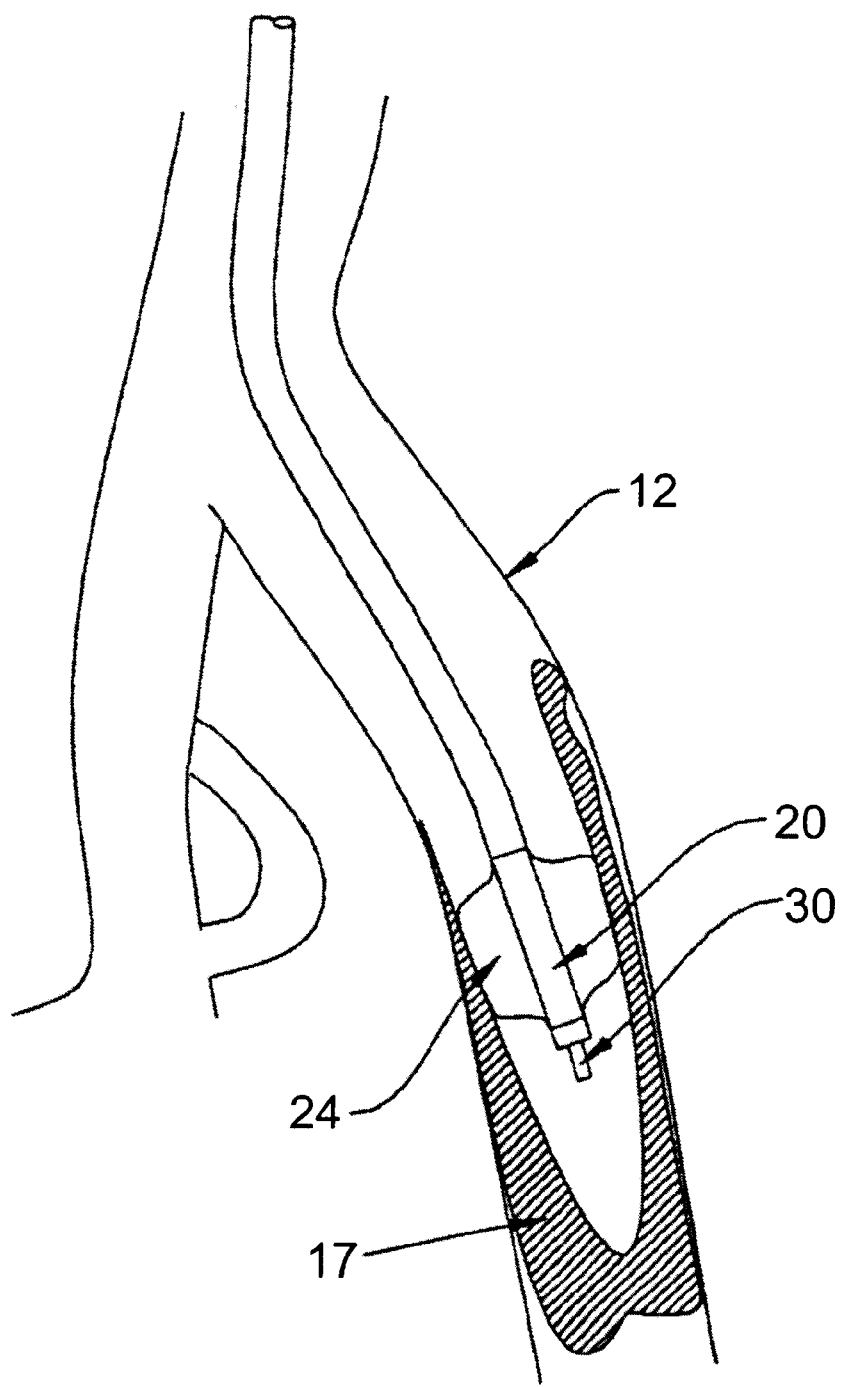

I. A 50 Year Old Male Having a Total Occlusion in the Superficial Femoral is Treated as Follows.
1. The patient is heparinized using standard procedures.
2. An introducer sheath is placed either in the same leg to provide retrograde access or in the opposite leg to provide cross-over access.
3. A guidewire is inserted and advanced to the site of the total occlusion.
4. The catheter device is inserted so that the distal end of the device is at the vascular site occupied by the total occlusion. The balloon is then inflated by depressing the syringe, such that the balloon occludes the vessel proximal to the occlusion. See FIG. 6.
5. Contrast medium is then injected into the vascular site to confirm the location of the distal end of the catheter and the inflated balloon.
6. A sufficient amount of heparinized phosphate buffered saline is then injected through port into the isolated vascular site or local environment and aspirated therefrom such that the isolated local environment is rendered substantially bloodless.
7. The surface of the total occlusion is then flushed with both an acidic dissolution fluid A (0.1N HCl, 0.05 M NaCl) and a phosphate buffered saline solution at the same time as shown in FIG. 6.
8. As the occlusion is demineralized, the catheter insert is advanced independent of the aspiration catheter and buffer catheter.
9. Where desired, the balloon may be deflated, the entire device repositioned, and then balloon may be reinflated to move the distal end of the total occlusion catheter insert to a site further into the occlusion. See FIGS. 7 and 8.
10. Once a passage through the occlusion sufficient to pass a guidewire through the occlusion is produced, the device is removed.
11. The above procedure results in fluid flow through the vascular site occupied by the lesion being reestablished, as evidenced by passing a guidewire through the vascular site.
12. Where desired, following reestablishment of fluid flow through the total occlusion, the total occlusion catheter insert is removed. A guidewire is then inserted through the large lumen of aspiration catheter 20 to a space beyond the distal end of the occlusion. A partial occlusion catheter insert is then introduced over the guidewire to a position such that the balloon at the distal end of the insert is on the far side of the partial occlusion. The vascular site is then flushed as shown in FIG. 4 until the desired amount of lesion dissolution is achieved.

II. Variations on the Above Procedure

Figure 9:
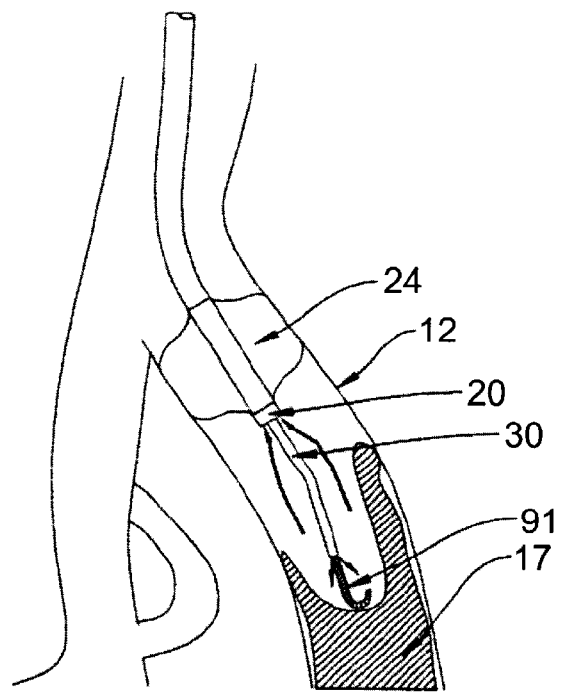
FIGS. 9 and 10 provide view of alternative embodiments of the subject methods in which external energy is applied to the occlusion, e.g. by movement of a guidewire as shown in FIG. 9.
Figure 10:
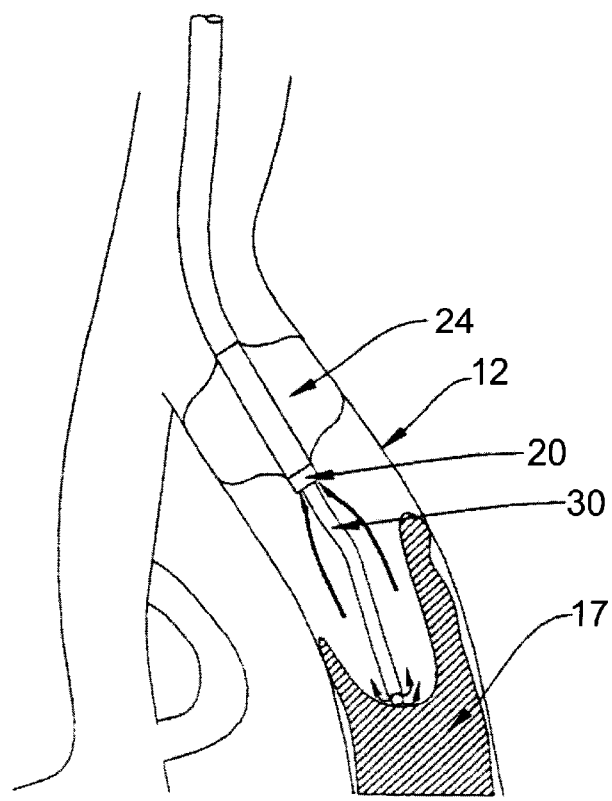

The above procedure is performed with the additional step of applying mechanical energy to the occlusion during flushing with the acidic dissolution solution. FIG. 9 shows mechanical energy being applied to the occlusion by contacting a guidewire 91 with the surface of the total occlusion during flushing. FIG. 10 shows mechanical energy being applied to the surface of the occlusion with the proximal end of the total occlusion insert. Other means of applying external energy, e.g. mechanical energy, may also be employed.

It is evident from the above discussion and results that improved methods of enhancing blood flow through a vascular occlusion are provided. Specifically, the subject invention provides a means for readily establishing fluid flow through a vascular site totally occluded by a calcified vascular occlusion, which has heretofore been difficult to practice. As such, the subject invention provides a means for using less traumatic procedures for treating peripheral vascular disease, thereby delaying or removing the need for graft procedures and/or amputation. A critical feature of the subject devices and methods is that only the target occlusion is subjected to the low pH conditions of the acidic dissolution solution. As such, unwanted contact of other portions of the target vascular site and/or host are avoided. As such, the subject invention represents a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A catheter device comprising:
   a first lumen in side of a first fluid delivery member that is open at its distal end and is in fluid communication with an acidic solution source;
   a second lumen inside of a second fluid delivery member that is open at its distal end and is in fluid communication with a buffer solution source; and
   a third lumen inside of an aspiration member that is open at its distal end, wherein said aspiration member includes a vascular occlusion means at its distal end;
   wherein said first, second and third lumens are coaxial and said first delivery member is movable relative to said second and third lumens.

2. The catheter device according to claim 1, wherein said second delivery member is moveable relative to said third lumen.

3. A catheter device comprising:
   (a) an inner first tubular member that is open at its distal end and is in fluid communication with an acidic solution source;
   (b) a middle second tubular member, wherein said second tubular member is open at its distal end and is in fluid communication with a buffer solution source; and
   (c) a third outer tubular member having a first vascular occlusion means, wherein said third tubular member is an aspiration member and is open at its distal end;
   wherein said tubular members are coaxial and are movable relative to each other, and further wherein each of said tubular members;
   (i) has a proximal and distal end; and
   (ii) comprises a lumen.

4. A catheter system comprising:
   (a) an aspiration catheter comprising an elongated tube having an aspiration lumen ending in an open distal end and art inflatable balloon at said distal end; and
   (b) a second elongated tube coaxially positioned inside of said aspiration catheter, wherein said second elongated tube is open at its distal end and is in fluid communication with a buffer solution source; and
   (c) both of:
       (i) a total occlusion catheter insert comprising an elongated tube having an open distal end; and
       (ii) a partial occlusion catheter insert consisting essentially of an elongated tube having a sealed distal end, an inflatable balloon at said distal end, and at least one infusion port proximal to said inflatable balloon;
       wherein said catheter inserts are in communication with an acidic solution source; and
   wherein at least said total and partial occlusion catheter inserts are capable of being slidably positioned within said second elongated tube to produce an annular space at the distal end of said elongated tube through which fluid may flow.

5. The catheter system according to claim 4, wherein said aspiration catheter is in fluid communication with a negative pressure source.

6. A system for enhancing fluid flow through a vascular site occupied by a vascular occlusion, said system comprising:
   (a) a catheter device according to claim 1;
   (b) a manifold;
   (c) an acidic fluid dissolution reservoir in fluid communication with said first lumen;
   (d) a buffer solution reservoir in fluid communication with said second lumen; and
   (e) a source of negative pressure in fluid communication with said third lumen.

7. The system according to claim 6, wherein said system further includes a balloon inflation means.

8. The system according to claim 2, wherein said balloon inflation means is a syringe.

9. The system according to claim 6, wherein said system further comprises a guidewire.

10. A kit for use in enhancing fluid flow through a vascular site occupied by a vascular occlusion, said kit comprising:
    a catheter device according to claim 1;
    art acidic dissolution solution; and
    a buffer solution.

11. The kit according to claim 10, wherein said kit comprises the system according to claim 4.

12. The kit according to claim 10, wherein said kit further a guidewire.

13. The kit according to claim 10, wherein said kit further comprises an imaging agent.

* * * * *